United States Patent
Utsumi et al.

(10) Patent No.: US 6,239,145 B1
(45) Date of Patent: May 29, 2001

(54) NITROXYL COMPOUNDS AND DRUGS AND REAGENTS CONTAINING THE SAME AS THE ACTIVE INGREDIENT

(75) Inventors: Hideo Utsumi; Hiroaki Sano, both of Fukuoka; Masaichi Naruse; Takashi Igarashi, both of Togane; Tetsuo Oi, Sakura, all of (JP)

(73) Assignee: Daiitchi Radioisotope Laboratories, Ltd., Tokyo (JP)

( * ) Notice: Subject to any disclaimer, the term of this patent is extended or adjusted under 35 U.S.C. 154(b) by 0 days.

(21) Appl. No.: 09/446,122

(22) PCT Filed: Jun. 26, 1998

(86) PCT No.: PCT/JP98/02868

§ 371 Date: Dec. 27, 1999

§ 102(e) Date: Dec. 27, 1999

(87) PCT Pub. No.: WO99/00365

PCT Pub. Date: Jan. 7, 1999

(30) Foreign Application Priority Data

Jun. 27, 1997 (JP) .................................................. 9-186082

(51) Int. Cl.$^7$ ...................... A61K 31/445; C07D 211/60; C07D 295/00
(52) U.S. Cl. ............................ 514/315; 546/245; 546/184
(58) Field of Search ..................... 546/245, 248, 546/184; 548/532, 535; 514/277, 423, 428, 315

(56) References Cited

FOREIGN PATENT DOCUMENTS

| 60-94960 | * | 5/1985 | (JP) . |
| 06239737 | * | 7/1997 | (JP) . |
| WO 91/13351 | | 9/1991 | (WO) . |
| WO 97/24145 A1 | * | 7/1997 | (WO) . |

OTHER PUBLICATIONS

Bowman, M. K. et. al., "Fourier–transform–EPR and low–frequency–EPR studies of nitroxides", Pure & Appl. Chem., vol. 62, No. 2, pp. 271–274, 1990.*

Greci, Lucedio et. al., "An attempt to evaluate hydroxyl end–groups in poly(butylene terephthalate" by spin–labeling technique, Polym. Bull., 10(7–8), pp. 362–367, 1983.*

Sosnovsky, G., et al: "A Study of the Favorskii Rearrangement with 3–Bromo–4–oxo–2,2,6,6–tetramethylpiperidin–1–oxyl", Journal of Organic Chem., vol. 60, No. 11 (1995), pp. 3414–3418, XP000940913.

Marc, G., et al., "A Short Way to Esters of 1–Oxy1–2,2,5,5–tetramethylpyrrolidine–3–carboxylic Acid by Favorski Rearrangement", Synthetic Communications, vol. 25, No. 7 (1995), pp. 1015–1021, XP000941142.

* cited by examiner

Primary Examiner—John Kight
Assistant Examiner—Binta Robinson
(74) Attorney, Agent, or Firm—Oblon, Spivak, McClelland, Maier & Neustadt, P.C.

(57) ABSTRACT

Nitroxyl compounds represented by general formula (I) which are usable in acquiring information about active oxygen or in vivo free radicals as biological images such as magnetic resonance images or magnetoencephalograms, wherein A represents hydrogen or —L—$(CH_2)_n$—OCOR (wherein L represents —COO— or -alkylene-COO—; and R represents $C_{1-4}$ alkyl); $R_1$, $R_2$, $R_3$, and $R_4$ represent each $C_{1-4}$ alkyl; and n is a number of from 1 to 4. Drugs and reagents containing the above compounds are usable in preventing, treating or diagnosing ischemic diseases, digestive diseases, cancer, cranial nervous diseases accompanied by nerve degeneration, inflammation, cataracts, or drug-induced organopathy.

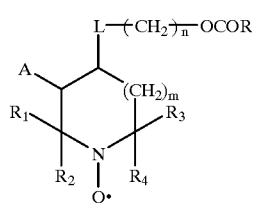

(I)

19 Claims, 1 Drawing Sheet

NITROXYL COMPOUNDS AND DRUGS AND REAGENTS CONTAINING THE SAME AS THE ACTIVE INGREDIENT

This is a 373 of PCT/JP98/02868 filed Jun. 26, 1998.

1. Technical Field

The present invention relates to novel nitroxyl compounds and drugs or reagents containing the same. More particularly, the present invention relates to novel nitroxyl compounds which are hydrolyzed in vivo, drugs usable in treating ischemic diseases, digestive diseases, cancer, cranial nervous diseases accompanied by nerve degeneration, inflammation, cataracts, or drug-induced organopathy caused by active oxygen or free radicals present in tissues, and reagents usable in diagnosing diseases relating to active oxygen or free radicals such as tumors and ischemic diseases by acquiring information about active oxygen or free radicals in the brain, heart, or other tissues as magnetic information.

2. Background Art

Active oxygen is defined as one type of oxygen species with a short life which is very reactive and takes part in various types of in vivo oxidation reactions. The scope of active oxygen varies depending on the definition. In a narrow sense, active oxygen means a hydroxyl radical (.OH), superoxide ($O_2^-$), singlet oxygen ($^1O_2$), and hydrogen peroxide ($H_2O_2$). In a broad sense, active oxygen includes a peroxy radical (LOO.) and alkoxy radical (LO.) which are derived from the reaction of the above active species and biological components such as unsaturated fatty acid L, and a hypochlorite ion ($ClO^-$) formed from $H_2O_2$ and $Cl^-$ by the reaction with myeloperoxidase and the like.

A hydroxyl radical, superoxide, peroxy radical, and alkoxy radical are all radicals. Radicals are defined as atoms or molecules which possess at least one unpaired electron. Singlet oxygen and hydrogen peroxide are not radicals, but are formed from a radical reaction or cause other radical reactions.

In recent years, active oxygen and free radicals showing various in vivo biological activities have attracted attention and have been studied in the field of biology, medicine, and pharmacology. Active oxygen and free radicals are formed in vivo due to ultraviolet rays, radiation, atmospheric pollution, oxygen, metal ions, ischemia-reperfusion, and the like.

Active oxygen and free radicals thus formed cause various in vivo reactions, for example, hyperoxidization of lipids, denaturation of proteins, and decomposition of nucleic acids. Ischemic diseases, digestive diseases, cancer, cranial nervous diseases accompanied by nerve degeneration, inflammation, cataracts, and drug-induced organopathy are known as diseases accompanied by such phenomena. Noninvasive detection of such active oxygen and in vivo free radicals which relate to so many diseases may help investigate the causes of a number of such diseases and provide useful medical information.

The following two methods have been known as a conventional method for detecting free radicals. One of them is an indirect method which comprises putting a reagent into a reaction system and detecting the resulting changes in absorbance or emission of light of the reaction system. Another method is an electron spin resonance (ESR) method which comprises directly detecting unpaired electrons of free radicals. The ESR method can measure both liquid samples and solid samples. Because even opaque or non-uniform samples can be measured by the ESR method, this method is very advantageous for detecting active oxygen in collected biological samples or in vivo.

However, a large amount biological samples could not be measured by conventional ESR devices utilizing microwaves of an X-band (about 9.5 GHz), which causes a great dielectric loss in water. In recent years, an ESR device utilizing low-frequency microwaves (300–2000 MHz) has been developed. This development enables the in vivo measurement of samples containing a large amount of water, in particular, free radicals in living body.

The principle of the biometry ESR method using nitroxyl compounds as a probe is as follows. Stable radicals administered in vivo are reduced by reaction with active oxygen or free radicals and lose paramagnetism. These signal changes are measured and analyzed to image active oxygen and in vivo free radicals non-invasively. Therefore, diagnostic reagents containing stable radical compounds as ESR contrast media are indispensable for performing the ESR method.

The principle of a nuclear magnetic resonance (NMR) method was discovered in 1945. Lauterbur first applied the NMR method to an imaging device for medicine (magnetic resonance imaging; MRI) in 1973. Since then, this diagnostic method has progressed remarkably and become one of the most universal diagnostic methods.

MRI first appeared as a diagnostic method using no contrast media. In order to increase detectability of a lesion site which is difficult to shade, utility of the contrast media has been recognized and contrast media are now generally used. Accompanied by this, contrast media exhibiting superior detectability have been demanded.

There are many nerve cells in the brain. Changes in electromotive force accompanied by activity of the nerve cells are widely used as an electronencephalogram (EEG; brain waves) Electric current, which flows in the nerves, caused by such an electromotive force forms magnetic fields in the circumference thereof. A record of the magnetic fields thus formed is referred to as a magnetoencephalogram (MEG). The strength and direction of the magnetic fields are determined depending on the position, strength, and direction of the electric current. Therefore, measurement of the brain magnetic fields is essentially equivalent to the measurement of electroencephalography. Electric conductivity of the living body is not constant and greatly varies depending on the tissue, bone, and the like. Moreover, only information of the electrical potential strength is obtained from the electronencephalogram. Because of this, it is difficult to precisely presume the active site.

A magnetoencephalogram measures changes of the magnetic fields caused by the magnetism of a living body. Because transmittance of the magnetic fields in the tissue is constant and almost equal to that in air, magnetic fields are not distorted, whereby the active site can be presumed precisely. However, the ratio of the magnetic field from the brain to geomagnetism is 1:100,000,000. Therefore, a magnetism sensor with high sensitivity is required and measurement is difficult. About 20 years ago, a fluxmeter using a superconducting quantum interference device (SQUID) was developed and enabled stable recording of the magnetism of a living body such as the brain for the first time. At present, medical instruments capable of non-invasively imaging the active site of the brain nerve cells from the outside have been developed.

This diagnostic method is used for discovering the focus of ictus epilepticus and has become an examination method useful for determining application of surgical treatment of epilepsy. This method is expected to be applied to the examination of initial symptoms of Alzheimer's disease in the future. However, since magnetic fields from the brain are extremely weak as described above, contrast media for magnetoencephalograms which compensate for the weak magnetic fields have been demanded.

If information about active oxygen and free radicals in tissue can be acquired as biological images by the non-invasive magnetic resonance measuring method, such information is useful for studying pathology in which active oxygen and free radicals take part, such as ischemic diseases, digestive diseases, cancer, cranial nervous diseases accompanied by nerve degeneration, inflammation, cataracts, and drug-induced organopathy (hereinafter referred to as "active oxygen related diseases") and diagnosing these diseases and symptoms.

In recent years, utility of nitroxyl compounds as contrast media for MRI and ESR and the antioxidation effect thereof have attracted attention. For example, paramagnetic inorganic compounds such as gadolinium are administered as contrast media in the MRI diagnosis in medicine in order to make a contrast for the lesion site. However, because of the toxicity of such compounds, nitroxyl compounds have been considered as new MRI contrast media instead of gadolinium. As ESR imaging has been developed and utility thereof has attracted attention, the utility value of nitroxyl compounds as imaging agents has increased. Furthermore, the possibility of using nitroxyl compounds as active oxygen scavenging agents has also been suggested (see, for example, J. Biol. Chem. 263:17921;1988).

However, since nitroxyl compounds available at present are unsatisfactory in their action such as distribution in vivo, nitroxyl compounds with superior properties as drugs have been demanded.

DISCLOSURE OF THE INVENTION

The present inventors have searched for stable radical compounds which can be used for acquiring information about active oxygen and in vivo free radicals as biological images by magnetic resonance or magnetoencephalograms. As a result, the inventors have found that specific nitroxyl compounds easily react with active oxygen or free radicals and produce an image of the brain tissue which has been difficult to contrast. Therefore, information about active oxygen and free radicals can be acquired as biological images by magnetic resonance and magnetoencephalogram. This finding has led to the completion of the present invention. Specifically, the present invention provides nitroxyl compounds shown by the following formula (I):

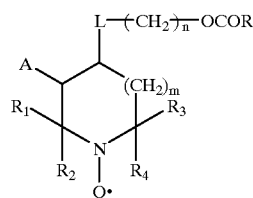

(I)

wherein A represents a hydrogen atom or the following group —L—(CH$_2$)$_n$—)OCOR, L represents —COO— or -alkylene-COO—, R, R$_1$, R$_2$, R$_3$, and R$_4$ represent an alkyl group having 1–4 carbon atoms, m represents an integer of 0 or 1, and n represents an integer from 1–4.

The present invention also provides drugs or reagents containing the above nitroxyl compound (I) as the active ingredient.

BEST MODE FOR CARRYING OUT THE INVENTION

Figure 1:
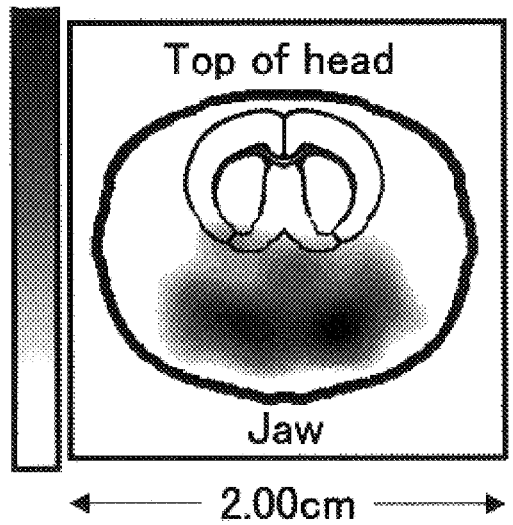
FIG. 1 shows an L-band ESR-CT image of a mouse brain in the case where 3-carboxy-PROXYL is used.

As examples of -alkylene-COO— for the group L in the nitroxyl compound of the present invention, a methylenecarbonyloxy group, ethylenecarbonyloxy group, tetramethylenecarbonyloxy group, methylethylenecarbonyloxy group, and the like can be given. As examples of the group R, a methyl group, ethyl group, butyl group, n-propyl group, i-propyl group, and the like can be given. As examples of R$_1$, R$_2$, R$_3$ and R$_4$, a methyl group, ethyl group, and the like can be given.

The nitroxyl compound (I) of the present invention is prepared by reacting a carboxyl group in nitrogen-containing cyclic oxylcarboxylic acid (II) with a halogenated ester compound (III) according to the following formula:

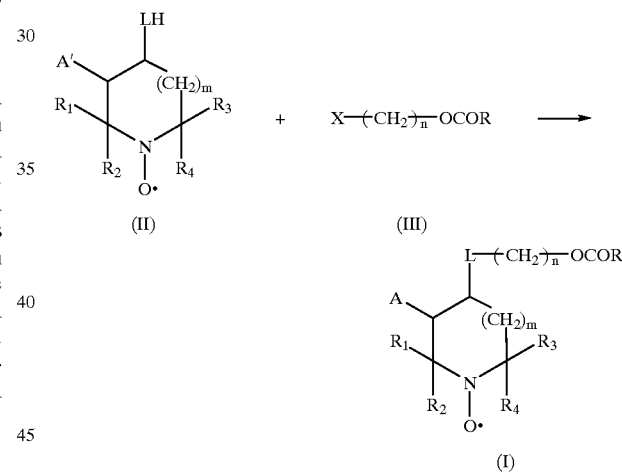

wherein X represents a halogen atom, A' represents a hydrogen atom or —LH, and A, L, R, R$_1$, R$_2$, R$_3$, R$_4$, m, and n are the same as defined above.

The nitrogen-containing cyclic oxylcarboxylic acid (II) and the halogenated ester compound (III) which are raw material compounds of the above reaction are known in the art or easily prepared according to a method of preparing such known compounds.

As specific examples of the nitrogen-containing cyclic oxylcarboxylic acid (II), 3-carboxy-2,2,5,5-tetramethylpyrrolidinyloxy, 3-(2-carboxy-1-methylethyl)-2,2,5,5-tetramethylpyrrolidinyloxy, 4-carboxy-2,2,6,6-tetramethylpiperidinyloxy, 4-(carboxymethyl)-2,2,6,6-tetramethylpiperidinyloxy, 4-(2-carboxyethyl)-2,2,6,6-tetramethylpiperidinyloxy, 3,4-dicarboxy-2,2,5,5-tetramethylpyrrolidinyloxy which are shown by the following formulas, and the like can be given.

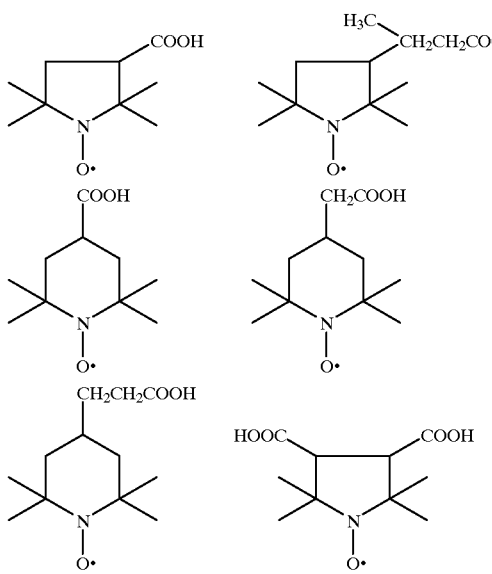

As examples of the halogenated ester compound (III), acetoxymethyl bromide, propionyloxymethyl bromide, n-butyryloxymethyl bromide, i-butyryloxymethyl bromide, acetoxyethyl bromide, propionyloxyethyl bromide, n-butyryloxyethyl bromide, and the like can be given.

The above reaction is an alkylation reaction of a carboxyl group and is carried out according to generally employed alkylation conditions for halides.

Drugs or reagents using the nitroxyl compound (I) of the present invention are prepared by dissolving the compound in a pharmaceutically or chemically acceptable solvent such as a physiological saline solution or isotonic phosphate buffer solution and adding optional components such as propylene glycol or benzyl alcohol as required.

Drugs or reagents using the nitroxyl compound (I) of the present invention are preferably prepared as injections, drops, liniments, eye drops, and the like.

As examples of the usage of the nitroxyl compound (I) of the present invention as drugs, diagnostic drugs can be given. Such diagnostic drugs are used as diagnostic drugs for active oxygen related diseases which detect the presence of active oxygen or free radicals by intravascular administration. For example, such diagnostic drugs are used for contrast media for MRI of the brain or heart diseases, magnetoencephalogram and ESR.

Such drugs are generally administered so that the amount of the nitroxyl compound (I) is 0.1–500 mg/kg, although the amount varies depending on the object or objective organs or diseases.

As examples of other usage for drugs, preventives or therapeutic agents for diseases caused by active oxygen or in vivo free radicals can be given. Since such preventives or therapeutic agents react with active oxygen or free radicals and eliminate them, these drugs are effective for prevention and treatment of the above-mentioned active oxygen related diseases.

By administering the above drugs to normal experimental animals and disease model experimental animals, active oxygen and free radicals generated from tissue or organs in a normal or diseased state can be detected and imaged from outside the body. From the results, these drugs can be used as detection reagents for determining what active oxygen and free radicals relate to what kind of diseases. These drugs provide useful medical information.

Furthermore, these drugs can be used as detection reagents for measuring the presence or absence or the amount of active oxygen or free radicals in tissue, by homogenizing collected samples, adding an appropriate buffer solution and the above drugs to the homogenized solution, allowing the mixture to react for a certain period of time, and measuring the ESR.

EXAMPLES

The present invention will be described in more detail by examples which should not be construed as limiting the present invention.

Example 1

Synthesis of Acetoxymethyl-2,2,5,5-tetramethylpyrrolidinyloxy-3-carboxylate:

(1) Synthesis of Acetoxymethyl Bromide 2.44 g of paraformaldehyde (granular, 81.2 mmol) was added to 6.0 ml of acetyl bromide (81.2 mmol) at room temperature. The mixture was stirred at 80° C. for 30 minutes. After confirming that the granules of paraformaldehyde had disappeared, the mixture was purified by atmospheric distillation (130–138° C., 750 mmHg) to obtain 4.54 g of acetylmethyl bromide as a light yellow oily substance (yield: 37%).

$^1$H-NMR: δ; 5.77 (2H, s), 2.12 (3H, s).

(2) Synthesis of Acetoxymethyl-2,2,5,5-tetramethylpyrrolidinyloxy-3-carboxylate 1 g of 3-carboxy-2,2,5,5-tetramethylpyrrolidinyloxy (5.37 mmol) (hereinafter may be abbreviated as "3-carboxy-PROXYL") was dissolved in 8 ml of dimethylformamide. After the addition of 0.74 ml of triethylamine (5.37 mmol) at room temperature, 1.31 g of acetoxymethyl bromide (8.18 mmol) was added at 0° C. The mixture was stirred at room temperature for 17 hours.

After the reaction mixture was diluted with 40 ml of dichloromethane, the mixture was washed with water and the water layer was extracted with 20 ml of dichloromethane. The organic layers were combined, washed with water, and dried ($MgSO_4$), and the solvent was evaporated. After the residue was purified by silica gel column chromatography (hexane-ethyl acetate, 2:1), recrystallization (ether-hexane) was performed to obtain 900 mg of acetoxymethyl-2,2,5,5-tetramethylpyrrolidinyloxy-3-carboxylate (3-carboxy-PROXYL acetoxymethyl ester) as a yellow lattice crystal (yield: 65%).

Melting point: 74–75° C.; IR(KBr):

3000, 2950, 2880, 1760, 1460, 1390, 1240, 1159, 1040, 840 ($cm^{-1}$); FAB-MASS (m/z; (relative strength)); 258 ($M^+$, 100), 244 ($M^+$—$CH_2$, 28), 186 (17), 172 (14), 154 (25), 136 (19), 111 (9).

Example 2

Acyloxyalkyl halides shown in Table 1 were obtained in the same manner as in Example 1 (1) except for replacing acetyl bromide with other acyl halides.

Nitroxyl derivatives shown in Table 1 were synthesized according to Example 1 (2) using these halides as raw materials.

TABLE 1

| Halide | Nitroxyl derivative |
|---|---|
| Propionyloxymethyl bromide | Propionyloxymethyl-2,2,5,5-tetramethylpyrrolidinyloxy-3-carboxylate |
| n-Butyryloxymethyl bromide | n-Butyryloxymethyl-2,2,5,5-tetramethylpyrrolidinyloxy-3-carboxylate |
| i-Butyryloxymethyl bromide | i-Butyryloxymethyl-2,2,5,5-tetramethylpyrrolidinyloxy-3-carboxylate |
| Acetoxyethyl bromide | Acetoxyethyl-2,2,5,5-tetramethylpyrrolidinyloxy-3-carboxylate |
| Propionyloxyethyl bromide | Propionyloxyethyl-2,2,5,5-tetramethylpyrrolidinyloxy-3-carboxylate |
| n-Butyryloxyethyl bromide | n-Butyryloxyethyl-2,2,5,5-tetramethylpyrrolidinyloxy-3-carboxylate |

Example 3

Nitroxyl derivatives shown in Table 2 were synthesized in the same manner as in Example 1 (2) using acyloxyalkyl halides prepared in Example 1 (1) and Example 2 which was according to Example 1 (1), except for using 3-(2-carboxy-1-methylethyl-2,2,5,5-tetramethylpyrrolidinyloxy instead of 3-carboxy-2,2,5,5-tetramethylpyrrolidinyloxy.

TABLE 2

| Halide | Nitroxyl derivative |
|---|---|
| Acetoxymethyl bromide | Acetoxymethyl-2-(2,2,5,5-tetramethylpyrrolidinyloxy-3-yl)butyrate |
| Propionyloxymethyl bromide | Propionyloxymethyl-2-(2,2,5,5-tetramethylpyrrolidinyloxy-3-yl)butyrate |
| n-Butyryloxymethyl bromide | n-Butyryloxymethyl-2-(2,2,5,5-tetramethylpyrrolidinyloxy-3-yl)butyrate |
| i-Butyryloxymethyl bromide | i-Butyryloxymethyl-2-(2,2,5,5-tetramethylpyrrolidinyloxy-3-yl)butyrate |
| Acetoxyethyl bromide | Acetoxyethyl-2-(2,2,5,5-tetramethylpyrrolidinyloxy-3-yl)butyrate |
| Propionyloxyethyl bromide | Propionyloxymethyl-2-(2,2,5,5-tetramethylpyrrolidinyloxy-3-yl)butyrate |
| n-Butyryloxyethyl bromide | n-Butyryloxymethyl-2-(2,2,5,5-tetramethylpyrrolidinyloxy-3-yl)butyrate |

Example 4

Nitroxyl derivatives shown in Table 3 were synthesized in the same manner as in Example 1 (2) using acyloxyalkyl halides prepared in Example 1 (1) and Example 2 which was according to Example 1 (1), except for using 4-carboxy-2,2,6,6-tetramethylpiperidinyloxy instead of 3-carboxy-2,2,5,5-tetramethylpyrrolidinyloxy.

TABLE 3

| Halide | Nitroxyl derivative |
|---|---|
| Acetoxymethyl bromide | Acetoxymethyl-2,2,6,6-tetramethylpiperidinyloxy-4-carboxylate |
| Propionyloxymethyl bromide | Propionyloxymethyl-2,2,6,6-tetramethylpiperidinyloxy-4-carboxylate |
| n-Butyryloxymethyl bromide | n-Butyryloxymethyl-2,2,6,6-tetramethylpiperidinyloxy-4-carboxylate |
| i-Butyryloxymethyl bromide | i-Butyryloxymethyl-2,2,6,6-tetramethylpiperidinyloxy-4-carboxylate |
| Acetoxyethyl bromide | Acetoxyethyl-2,2,6,6-tetramethylpiperidinyloxy-4-carboxylate |
| Propionyloxyethyl bromide | Propionyloxyethyl-2,2,6,6-tetramethylpiperidinyloxy-4-carboxylate |
| n-Butyryloxyethyl bromide | n-Butyryloxyethyl-2,2,6,6-tetramethylpiperidinyloxy-4-carboxylate |

Example 5

Nitroxyl derivatives shown in Table 4 were synthesized in the same manner as in Example 1 (2) using acyloxyalkyl halides prepared in Example 1 (1) and Example 2 which was according to Example 1 (1), except for using 4-(carboxymethyl)-2,2,6,6-tetramethylpiperidinyloxy instead of 3-carboxy-2,2,5,5-tetramethylpyrrolidinyloxy.

TABLE 4

| Halide | Nitroxyl derivative |
|---|---|
| Acetoxymethyl bromide | Acetoxymethyl-2,2,6,6-tetramethylpiperidinyloxy-4-acetate |
| Propionyloxymethyl bromide | Propionyloxymethyl-2,2,6,6-tetramethylpiperidinyloxy-4-acetate |
| n-Butyryloxymethyl bromide | n-Butyryloxymethyl-2,2,6,6-tetramethylpiperidinyloxy-4-acetate |
| i-Butyryloxymethyl bromide | i-Butyryloxymethyl-2,2,6,6-tetramethylpiperidinyloxy-4-acetate |
| Acetoxyethyl bromide | Acetoxyethyl-2,2,6,6-tetramethylpiperidinyloxy-4-acetate |
| Propionyloxyethyl bromide | Propionyloxyethyl-2,2,6,6-tetramethylpiperidinyloxy-4-acetate |
| n-Butyryloxyethyl bromide | n-Butyryloxyethyl-2,2,6,6-tetramethylpiperidinyloxy-4-acetate |

Example 6

Nitroxyl derivatives shown in Table 5 were synthesized in the same manner as in Example 1 (2) using acyloxyalkyl halides prepared in Example 1 (1) and Example 2 which was according to Example 1 (1), except for using 4-(2-carboxyethyl)-2,2,6,6-tetramethylpiperidinyloxy instead of 3-carboxy-2,2,5,5-tetramethylpyrrolidinyloxy.

TABLE 5

| Halide | Nitroxyl derivative |
| --- | --- |
| Acetoxymethyl bromide | Acetoxymethyl-2-(2,2,6,6-tetramethylpiperidinyloxy-4-yl)propionate |
| Propionyloxymethyl bromide | Propionyloxymethyl-2-(2,2,6,6-tetramethylpiperidinyloxy-4-yl)propionate |
| n-Butyryloxymethyl bromide | n-Butyryloxymethyl-2-(2,2,6,6-tetramethylpiperidinyloxy-4-yl)propionate |
| i-Butyryloxymethyl bromide | i-Butyryloxymethyl-2-(2,2,6,6-tetramethylpiperidinyloxy-4-yl)propionate |
| Acetoxyethyl bromide | Acetoxyethyl-2-(2,2,6,6-tetramethylpiperidinyloxy-4-yl)propionate |
| Propionyloxyethyl bromide | Propionyloxyethyl-2-(2,2,6,6-tetramethylpiperidinyloxy-4-yl)propionate |
| n-Butyryloxyethyl bromide | n-Butyryloxyethyl-2-(2,2,6,6-tetramethylpiperidinyloxy-4-yl)propionate |

Example 7

Nitroxyl derivatives shown in Table 6 were prepared in the same manner as in Example 1 (2) using acyloxyalkyl halides prepared in Example 1 (1) and Example 2 which was according to Example 1 (1), except for using 3,4-dicarboxy-2,2,5,5-tetramethylpyrrolidinyloxy instead of 3-carboxy-2,2,5,5-tetramethylpyrrolidinyloxy.

TABLE 6

| Halide | Nitroxyl derivative |
| --- | --- |
| Acetoxymethyl bromide | 3,4-bis(acetoxymethyl)-2,2,5,5-tetramethylpyrrolidinyloxy-3,4-dicarboxylate |
| Propionyloxymethyl bromide | 3,4-bis(propionyloxymethyl)-2,2,5,5-tetramethylpyrrolidinyloxy-3,4-dicarboxylate |
| n-Butyryloxymethyl bromide | 3,4-bis(n-butyryloxymethyl)-2,2,5,5-tetramethylpyrrolidinyloxy-3,4-dicarboxylate |
| i-Butyryloxymethyl bromide | 3,4-bis(i-butyryloxymethyl)-2,2,5,5-tetramethylpyrrolidinyloxy-3,4-dicarboxylate |
| Acetoxyethyl bromide | 3,4-bis(acetoxyethyl)-2,2,5,5-tetramethylpyrrolidinyloxy-3,4-dicarboxylate |
| Propionyloxyethyl bromide | 3,4-bis(propionyloxyethyl)-2,2,5,5-tetramethylpyrrolidinyloxy-3,4-dicarboxylate |
| n-Butyryloxyethyl bromide | 3,4-bis(n-butyryloxyethyl)-2,2,5,5-tetramethylpyrrolidinyloxy-3,4-dicarboxylate |

Example 8

Synthesis of Trans-3,4-bis(acetoxymethyl)-2,2,5,5-tetramethylpyrrolidinyloxy-3,4-dicarboxylate:
(1) Synthesis of 3-cyano-2,2,5,5-tetramethyl-3-pyrroline-1-yloxy:

3-carbamoyl-2,2,5,5-tetramethyl-3-pyrroline-1-yloxy (ALDRICH 15,568-3) was dissolved in 6 ml of pyridine. After the addition of 3.26 g of p-toluenesulfonyl chloride (17.1 mmol) at room temperature, the mixture was stirred at room temperature for 20 hours. After the addition of 30 ml of a 4% sodium hydroxide aqueous solution, the mixture was stirred at 80° C. for 10 minutes. The reaction mixture was diluted with 20 ml of ether and washed with a 10% hydrochloric acid aqueous solution (10 ml×1). After extracting the water layer with ether (10 ml×1), the organic layers were combined, washed with a saturated sodium bicarbonate aqueous solution (10 ml×1) and water, and dried (MgSO$_4$), and the solvent was evaporated. The residue was purified by silica gel column chromatography (hexane-ethyl acetate, 1:1) and recrystallization (hexane) to obtain 1.46 g of 3-cyano-2,2,5,5-tetramethyl-3-pyrroline-1-yloxy as a yellow needle crystal (yield: 89%).

Melting point: 52–53° C.; IR: 3080, 2990, 2240, 1460, 1440, 1370, 1340, 1280, 1160 cm$^{-1}$.
(The above IR values were measured by dropping a sample dichloromethane solution onto a disposable IR sheet and removing dichloromethane by volatilization.)
(2) Synthesis of 3,4-dicyano-2,2,5,5-tetramethylpyrrolidinyloxy 145 ml of dimethylformamide and 140 ml of water were added to 7.10 g of 3-cyano-2,2,5,5-tetramethyl-3-pyrroline-1-yloxy (43.0 mmol) to prepare a homogeneous solution. 5.60 g of potassium cyanide (86.0 mmol) and 4.60 g of ammonium chloride (86.0 mmol) were added at room temperature and the mixture was stirred at 70° C. for three hours. The mixture was then stirred at room temperature for three days.

After extracting the reaction mixture with ether (200 ml), this mixture was washed with a saturated sodium bicarbonate aqueous solution (2×50 ml) and water, and dried (MgSO$_4$), followed by evaporation of the solvent. The residue was purified by silica gel column chromatography (hexane-ethyl acetate, 2:1). A yellow plate crystal obtained from the first fraction was purified by recrystallization (dichloromethane-hexane) to obtain 2.95 g of trans-3,4-dicyano-2,2,5,5-tetramethylpyrrolidinyloxy (yield: 36%).

Melting point: 142–143° C.; IR(KBr): 3000, 2950, 2910, 2250, 1470, 1440, 1395, 1390, 1305, 1280, 1250, 1190, 1140, 1060 cm$^{-1}$.

1.64 g of cis-3,4-dicyano-2,2,5,5-tetramethylpyrrolidinyloxy (yield: 20%) was obtained from the second fraction as a yellow lattice crystal. It was difficult to purify this product further by recrystallization due to the low crystallization rate.

Melting point: 81–82° C.; IR(KBr): 3000–2960, 2260, 1470, 1460, 1400, 1395, 1390, 1330, 1295, 1250, 1195, 1180, 1160, 1135, 1080, 1060 cm$^{-1}$.
(3) Synthesis of Trans-3,4-bis(acetoxymethyl)-2,2,5,5-tetramethylpyrrolidinyloxy-3,4-dicarboxylate 2.95 g of trans-3,4-dicyano-2,2,5,5-tetramethylpyrrolidinyloxy (15.3 mmol) was dissolved in 30 ml of methanol. After the addition of 30 ml of a 2N-sodium hydroxide aqueous solution, the mixture was stirred at 80° C for six hours.

A 1N-hydrochloric acid aqueous solution was added to the reaction mixture to adjust the pH to 1, and the solvent was then evaporated. A dichloromethane-methanol (2:1) mixed solvent was added to the residue, and the soluble components were purified by silica gel column chromatography (dichloromethane-methanol, 2:1) to obtain 4.50 g of trans-3,4-dicarboxy-2,2,5,5-tetramethylpyrrolidinyloxy as a yellow oily substance. Because it was difficult to purify this product further due to the high water solubility, acetoxymethylation was then performed.

4.50 g of crude trans-3,4-dicarboxy-2,2,5,5-tetramethylpyrrolidinyloxy was dissolved in 80 ml of dimethylformamide. After the addition of 5.41 ml of triethylamine (39.0 mmol) at room temperature, 10.7 g of acetoxymethyl bromide (70.2 mmol) was added at 0° C. The mixture was then stirred at room temperature for seven days.

The reaction mixture was diluted with 200 ml of dichloromethane and washed with water. After extracting the water layer with 50 ml of dichloroethane, the organic layers were combined, washed with water, and dried (MgSO$_4$). The solvent was then evaporated. The residue was purified by silica gel column chromatography (hexane-ethyl acetate, 1:1) and recrystallized (dichloromethane-diisopropyl ether) to obtain 1.16 g of trans-3,4-bis(acetoxymethyl)-2,2,5,5-tetramethylpyrrolidinyloxy-3,4-dicarboxylate as a yellow needle crystal.

Melting point: 127–129° C.; IR(KBr): 3450, 3170, 2980, 2940, 1760, 1710, 1700, 1630, 1460–1405, 1380–1360, 1300, 1240, 1190–1140, 1100, 1050, 1005–960 cm$^{-1}$.

FAB-MASS (m/z; (relative strength)); 375 (MH$^+$, 50), 345 (29), 301 (100), 212 (56), 139 (83).

Example 9

Synthesis of Cis-3,4-bis(acetoxymethyl)-2,2,5,5-tetramethylpyrrolidinyloxy-3,4-dicarboxylate:

1.64 g of cis-3,4-dicyano-2,2,5,5-tetramethylpyrrolidinyloxy (8.53 mmol), which was synthesized as an intermediate material in Example 8, was dissolved in 16 ml of methanol. After the addition of 16 ml of a 2N-sodium hydroxide aqueous solution, the mixture was stirred at 80° C. for six hours.

A 1N-hydrochloric acid aqueous solution was added to the reaction mixture to adjust the pH to 1, and the solvent was evaporated. After the addition of a dichloromethane-methanol (2:1) mixed solvent to the residue, the soluble components were purified by silica gel column chromatography (dichloromethane-methanol, 2:1) to obtain 2.27 g of cis-3,4-dicarboxy-2,2,5,5-tetramethylpyrrolidinyloxy as a yellow oily substance. Because it was difficult to purify this product further due to the high water solubility, acetoxymethylation was then performed.

2.27 g of crude cis-3,4-dicarboxy-2,2,5,5-tetramethylpyrrolidinyloxy was dissolved in 18 ml of dimethylformamide. After the addition of 2.36 ml of triethylamine (17.1 mmol) at room temperature, 4.70 g of acetoxymethyl bromide (30.7 mmol) was added at 0° C. The mixture was stirred at room temperature for seven days. The reaction mixture was diluted with 50 ml of dichloromethane and washed with water. After extracting the water layer with 20 ml of dichloromethane, the organic layers were combined, washed with water, and dried (MgSO$_4$), and the solvent was evaporated. The residue was purified by silica gel column chromatography (hexane-ethyl acetate, 1:1) to obtain 264 mg of cis-3,4-bis(acetoxymethyl)-2,2,5,5-tetramethylpyrrolidinyloxy-3,4-15 dicarboxylate as a yellow oily substance.

Example 10

Synthesis of 3,4-bis(acetoxymethyl)-2,2,5,5-tetramethylpyrrolidinyloxy-3,4-dicarboxylate:
(1) Synthesis of 3,4-dicyano-2,2,5,5-tetramethylpyrrolidinyloxy 20 ml of dimethylformamide and 210 ml of water were added to 11.91 g of 3-cyano-2,2,5,5-tetramethyl-3-pyrroline-1-yloxy (72.1 mmol) to prepare a homogeneous solution. 9.39 g of potassium cyanide (144 mmol) and 7.71 g of ammonium chloride (144 mmol) were added to the mixture at room temperature. The mixture was stirred at 70° C. for three hours and then stirred at room temperature for three days.

After diluting the reaction mixture with 300 ml of ether, the mixture was washed with a saturated sodium bicarbonate aqueous solution (2×50 ml), then with water, and dried (MgSO$_4$), and the solvent was evaporated. The residue was purified by silica gel column chromatography (hexane-ethyl acetate, 2:1) to obtain 10.52 g of 3,4-dicyano-2,2,5,5-tetramethylpyrrolidinyloxy (yield: 76%). The trans and cis forms did not separate during the purification. The purified product was obtained while maintaining the diastereomer ratio caused by the reaction (trans form:cis form=1.8:1). (2) Synthesis of 3,4-bis(acetoxymethyl)-2,2,5,5-tetramethylpyrrolidinyloxy-3,4-dicarboxylate:

10.52 g of 3,4-dicyano-2,2,5,5-tetramethylpyrrolidinyloxy (54.7 mmol) was dissolved in 100 ml of methanol. 100 ml of a 4% sodium hydroxide aqueous solution was added to the mixture. The mixture was stirred at 80° C. for six hours. A 1N-hydrochloric acid aqueous solution was added to the reaction mixture to adjust the pH to 1, and the solvent was evaporated. The residue was purified with dichloromethane-methanol (2:1) to obtain 11.62 g of 3,4-dicarboxy-2,2,5,5-tetramethylpyrrolidinyloxy as a yellow oily substance. Because it was difficult to purify this product further due to the high water solubility, acetoxymethylation was then performed.

11.62 g of crude 3,4-dicarboxy-2,2,5,5-etramethylpyrrolidinyloxy was dissolved in 18 ml of dimethylformamide. After the addition of 2.36 ml of triethylamine (17.1 mmol) at room temperature, 4.70 g of acetoxymethyl bromide (30.7 mmol) was added at 0° C. The mixture was then stirred at room temperature for seven days.

The reaction mixture was diluted with 50 ml of dichloromethane and washed with water. After extracting the water layer with 20 ml of dichloromethane, the organic layers were combined, washed with water, and dried (MgSO$_4$), and the solvent was evaporated. The residue was purified by silica gel column chromatography (dichloromethane-methanol, 2:1) to obtain 2.42 g of 3,4-bis(acetoxymethyl)-2,2,5,5-tetramethylpyrrolidinyloxy-3,4-dicarboxylate as a yellow oily substance (yield from 3,4-dicyano-2,2,5,5-tetramethylpyrrolidinyloxy: 12%). IR (IR sheet): 3480–3200, 3000, 2940, 2880, 1780–1620, 1480–1360, 1240, 1160, 840, 740 cm$^{-1}$.

Example 11

Synthesis of acetoxymethyl-2,2,6,6-tetramethylpyperidinyloxy-4-carboxylate:

100 mg of 4-carboxy-2,2,6,6-tetramethylpiperidinyloxy (ALDRICH 38,200-0) (0.499 mmol) was dissolved in 1 ml of dimethylformamide. After the addition of 0.069 ml of triethylamine (0.499 mmol) at room temperature, 137 mg of acetoxymethyl bromide (0.898 mmol) was added at 0° C. The mixture was stirred at room temperature for seven days.

After diluting the reaction mixture with dichloromethane (5 ml), the mixture was washed with water and dried (MgSO$_4$), and the solvent was evaporated. The residue was purified by silica gel column chromatography (hexane-ethyl acetate, 2:1) to obtain 43.2 mg of acetoxymethyl-2,2,6,6-tetramethylpiperidinyloxy-4-carboxylate as a pale red fine needle crystal (yield: 32%).

Melting point: 67–68° C.; IR(KBr): 2980, 2950, 1760, 1740, 1380, 1375, 1380, 1375, 1310, 1300, 1240, 1200, 1170, 1070, 1010, 995, 980 cm$^{-1}$.

FAB-MASS (m/z; (relative strength)); 272 (M$^+$, 100), 258 (M$^+$-CH$_2$, 56), 256 (14), 242 (7), 200(39), 184 (18), 154 (11), 136 (12), 123 (11), 114 (10).

Example 12

Hydrolysis Test:

Changes with time in the hydrolysis rate of 3-carboxy-PROXYL methyl ester and 3-carboxy-PROXYL acetoxymethyl ester by an esterase were examined.

200 μl of a 10 mM test sample solution was mixed with 800 μl of 5 micro units of an esterase (carboxy esterase, carboxylic ester hydrolase; EC 3.1.1.1 manufactured by Sigma, catalogue No. E3128). The mixture was incubated at 37° C. for 10 seconds, 1 minute, 3 minutes, 5 minutes, 10 minutes, and 30 minutes, respectively. The mixture was then analyzed by HPLC to calculate the hydrolysis rate from the amount ratio of the unchanged product to 3-carboxy-PROXYL which is a hydrolysate thereof.

HPLC was performed using a UV-VIS detector (UV-8020), a dual pump (CCPS), a column (ODS-80Ts), and a TSK precolumn (BSA-ODS) all manufactured by Tosoh Corp.

[Measurement conditions of HPLC]

UV wavelength: 245 nm

Mobile phase: 20 mM phosphate buffer solution (pH 2.2)/methanol=60/40

Flow rate: 0.5 ml/min.

Temperature: 20–25° C.

Injection volume: 20 μl

[Result]

Table 7 shows the changes with time in the hydrolysis rate of the test samples by an esterase.

TABLE 7

| | Hydrolysis Rate (%) | | | | | |
|---|---|---|---|---|---|---|
| Test Sample | 10 sec. | 1 min. | 3 min. | 5 min. | 10 min. | 30 min. |
| 3-carboxy-PROXYL methyl ester | 0.05 ± 0.43 | 0.40 ± 0.34 | 0.80 ± 0.49 | 1.35 ± 0.49 | 2.54 ± 0.08 | 8.25 ± 1.51 |
| 3-carboxy-PROXYL acetoxymethyl ester | 30.1 ± 11.9 | 70.8 ± 3.4 | 93.9 ± 1.1 | 96.7 ± 2.2 | 100.0 ± 0.0 | 100.0 ± 0.0 |

Mean ± standard deviation (n = 3)

As shown in Table 7, 3-carboxy-PROXYL acetoxymethyl ester was slightly hydrolyzed after 10 seconds, and the ratio increased to about 90% in 3 minutes and to almost 100% in 10 minutes.

The hydrolysis rate of 3-carboxy-PROXYL methyl ester was 10% or less after 30 minutes. From these results, 3-carboxy-PROXYL acetoxymethyl ester was confirmed to be hydrolyzed by an esterase in a shorter period of time than 3-carboxy-PROXYL methyl ester.

Example 13

Organ distribution:

The organ distribution was tested by ESR using 3-carboxy-PROXYL, 3-carboxy-PROXYL methyl ester, 3-carboxy-PROXYL ethyl ester, 2-ethyl-2,5,5-trimethyloxazolidinyloxy, and 3-carboxy-PROXYL acetoxymethyl ester as test samples.

The test was performed using sixteen groups of three mice each (ddY, female) as experimental animals as described below. 7.5 μmol of the test samples (2.5 μmol for 3-carboxy-PROXYL acetoxymethyl ester) were administered to the vena caudalis of the mice under ether, and allowed to stand for 3, 10, and 30 minutes, respectively. The mice were then dehematized quickly and the brain was removed. The brain was homogenized with a phosphate buffer solution in an amount nine times that of the removed brain. The blood was diluted with a phosphate buffer solution in an amount nine times thereof. A potassium ferricyanide solution was added to part of the tissue thus treated so that the final concentration was 1 mM. The test samples which had become hydroxylamines by the active oxygen and the like in vivo were converted to nitroxide radicals (one electron oxidation) to prepare ESR samples.

The concentration of the test samples after one electron oxidation was measured by x-band ESR and determined as the concentration of the samples in vivo. The test sample solution in an amount equal to that administered to the mice was prepared. This solution was treated in the same way, beginning from the addition of the nine-fold phosphate buffer solution. The concentration of the test sample was measured by x-band ESR and was determined as the total dosage. 15 mm of each sample taken into a 100 μl capillary (length 116.5 mm) was put into a quartz cell to measure the ESR spectrum under the following conditions.

(Measurement conditions)

Measuring device: Electron spin resonance spectrometry "JES-RE1X" (manufactured by JEOL Ltd.)

Magnetic field: 331.5±5 mT

Magnetic field modulation: 100 kHz

Modulation width: 0.1 mT

Time constant: 0.03 second

Microwave power: 5 mW

Sweep time: 2 minutes

Measurement temperature: room temperature

[Result]

The ratio of the test samples in the brain and blood to the total dosage (% dose), the value obtained by dividing the % dose by the weight of the brain and blood (% dose/g), and the ratio of the % dose/g of the brain, which was the target organ, to the % dose/g of the blood were calculated from the ESR spectrum. The results are shown in Tables 8, 9, and 10.

TABLE 8

| | Brain (% dose) | | | Blood (% dose) | | |
|---|---|---|---|---|---|---|
| Test Sample | 3 min. | 10 min. | 30 min. | 3 min. | 10 min. | 30 min. |
| 3-carboxy-PROXYL | 0.05 | 0.30 | 0.16 | 14.06 | 6.14 | 3.89 |
| 3-carboxy-PROXYL methyl ester | 1.31 | 0.67 | 0.21 | 4.62 | 2.68 | 2.18 |
| 3-carboxy-PROXYL ethyl ester | 0.79 | 0.74 | 0.12 | 3.46 | 2.92 | 3.38 |
| 2-ethyl-2,5,5-trimethyloxazolidinyloxy | 1.63 | 1.64 | 0.52 | 4.52 | 3.69 | 0.81 |
| 3-carboxy-PROXYL acetoxymethyl ester | 2.26 | 2.77 | 1.98 | 6.28 | 4.41 | 4.21 |

TABLE 9

| | Brain (% dose/g) | | | Blood (% dose/g) | | |
|---|---|---|---|---|---|---|
| Test Sample | 3 min. | 10 min. | 30 min. | 3 min. | 10 min. | 30 min. |
| 3-carboxy-PROXYL | 0.13 | 0.69 | 0.41 | 7.89 | 4.43 | 2.58 |
| 3-carboxy-PROXYL methyl ester | 3.14 | 1.82 | 0.48 | 2.48 | 1.74 | 1.36 |

TABLE 9-continued

| Test Sample | Brain (% dose/g) | | | Blood (% dose/g) | | |
|---|---|---|---|---|---|---|
| | 3 min. | 10 min. | 30 min. | 3 min. | 10 min. | 30 min. |
| 3-carboxy-PROXYL ethyl ester | 1.89 | 1.84 | 0.28 | 2.02 | 2.20 | 2.11 |
| 2-ethyl-2,5,5-trimethyloxazolidinyloxy | 3.81 | 4.12 | 1.21 | 2.55 | 2.32 | 1.30 |
| 3-carboxy-PROXYL acetoxymethyl ester | 5.80 | 7.17 | 5.82 | 3.26 | 2.21 | 2.02 |

TABLE 10

| Test Sample | Ratio of brain to blood | | |
|---|---|---|---|
| | 3 min. | 10 min. | 30 min. |
| 3-carboxy-PROXYL | 0.02 | 0.16 | 0.03 |
| 3-carboxy-PROXYL methyl ester | 1.27 | 1.05 | 0.14 |
| 3-carboxy-PROXYL ethyl ester | 0.94 | 0.84 | 0.05 |
| 2-ethyl-2,5,5-trimethyloxazolidinyloxy | 1.50 | 1.78 | 1.72 |
| 3-carboxy-PROXYL acetoxymethyl ester | 1.78 | 3.14 | 2.88 |

As is clear from these results, three compounds including 3-carboxy-PROXYL methyl ester, 3-carboxy-PROXYL ethyl ester, and 2-ethyl-2,5,5-trimethyloxazolidinyloxy exhibited a high brain to blood ratio of 0.84–1.78 after 10 minutes compared to 3-carboxy-PROXYL which exhibited 0.16.

3-carboxy-PROXYL acetoxymethyl ester, which is the compound of the present invention, exhibited a still higher value of 3.14. Moreover, in comparison with the above three compounds which exhibited a rapid decrease in the accumulation in the brain with time, 3-carboxy-PROXYL acetoxymethyl ester exhibited a high value of 2.88 after 30 minutes.

Although the reason for this long duration of the brain accumulation rate has not been fully clarified, it is presumed to be as follows. The —COO— site in the group L of the compound of the present invention is easily hydrolyzed by an esterase. This site becomes —COO$^-$ in the brain and the compound itself has an electric charge. Therefore, the redistribution from the brain to the blood can be inhibited.

Example 14

Measurement of L Band ESR-CT Image of Mouse Brain 2.5 μmol of 3-carboxy-PROXYL, 3-carboxy-PROXYL methyl ester, and acetoxymethyl-2,2,5,5-tetramethylpyrrolidinyloxy-3-carboxylate were administered to the vena caudalis of the mice which were anesthetized with Nembutal (75 mg/kg, intramuscular injection). An L band ESR-CT image of the head axial transverse section was measured under the following conditions.

[Measurement conditions of L band ESR-CT]

Measuring device: Electron spin resonance spectrometry "JES-RE31" (manufactured by JEOL Ltd.)
Magnetic field: 38.5 mT
Magnetic field gradient: 0.45 mT/cm
Sweep width: 1.49mT
Sampling point: 5
Integration frequency: 5
Projection: 18 (every 10°)
Magnetic field modulation: 100 kHz
Modulation width: 0.2 mT
Time constant: 0.003 second
Microwave power: 5.0 mW
Measurement temperature: room temperature

[Result]

Figure 2:
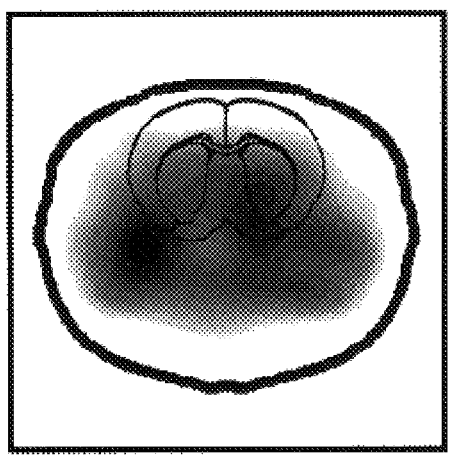
FIG. 2 shows an L-band ESR-CT image of a mouse brain in the case where 3-carboxy-PROXYL methyl ester is used.
Figure 3:
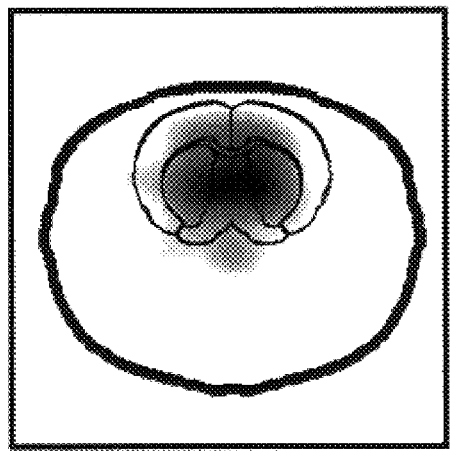
FIG. 3 shows an L-band ESR-CT image of a mouse brain in the case where acetoxymethyl 2,2,5,5-tetramethylpyrrolidinyloxy-3-carboxylate is used.

The L band ESR-CT images of the mouse brain to which 3-carboxy-PROXYL or 3-carboxy-PROXYL methyl ester was administered as control are respectively shown in FIGS. 1 and 2. The L band ESR-CT image of the mouse brain to which acetoxymethyl-2,2,5,5-tetramethylpyrrolidinyloxy-3-carboxylate of the present invention was administered is shown in FIG. 3.

As is clear from these results, 3-carboxy-PROXYL was highly concentrated outside the brain and scarcely shifted inside the brain. 3-Carboxy-PROXYL methyl ester was concentrated outside the brain, but was also highly concentrated inside the brain. Acetoxymethyl- 2,2,5,5-tetramethylpyrrolidinyloxy-3-carboxylate exhibited decreased accumulation outside the brain and was still more highly concentrated inside the brain, whereby a clear L band ESR-CT image of the mouse brain was obtained.

INDUSTRIAL APPLICABILITY

The nitroxyl compounds of the present invention which are active ingredients of the diagnostic agent have enough half-life and interact with active oxygen or in vivo free radicals. Therefore, the nitroxyl compounds are useful for acquiring biological images of the distribution of free radicals by a magnetic resonance method. Accordingly, the diagnostic agent can be used for diagnosing active oxygen related diseases such as ischemic diseases, digestive diseases, cancer, cranial nervous diseases accompanied by nerve degeneration, inflammation, cataracts, or drug-induced organopathy in which active oxygen or free radicals take part.

Specifically, the above active oxygen related diseases can be diagnosed by administering the diagnostic agent containing the nitroxyl compounds of the present invention to the living body, and detecting the signal change of the nitroxyl compounds in vivo by ESR, NMR, and the like.

In particular, because the nitroxyl compounds of the present invention pass through the brain blood barrier and interact with free radicals in the brain, cerebral ischemia and brain tumors of which imaging by a magnetic resonance method has been difficult can be imaged.

Therefore, the diagnostic agent of the present invention is used for MRI and magnetoencephalograms. If ESR devices capable of measuring large content biological samples such as a human head are developed, the diagnostic agent non-invasively diagnoses the diseases or symptoms in which active oxygen or free radicals take part by acquiring the images of free radical distribution in the brain by the ESR method. The nitroxyl compounds of the present invention react with active oxygen or in vivo free radicals and eliminate them. Therefore, the nitroxyl compounds can be used as preventives or therapeutic agents for active oxygen related diseases such as ischemic diseases, digestive diseases, cancer, cranial nervous diseases accompanied by nerve degeneration, inflammation, cataracts, or drug-induced organopathy in which active oxygen or free radicals take part.

The nitroxyl compounds detect and image active oxygen and free radicals generated from tissue or organs in a normal or diseased state from the outside of the body by administration of the compounds to normal experimental animals and disease model experimental animals. From the results, these drugs can be used as detection reagents for detecting what active oxygen and free radicals relate to what kind of diseases, whereby useful medical information is obtained.

Furthermore, the presence or absence or the amount of active oxygen or free radicals in tissue can be measured by homogenizing collected samples, adding an appropriate buffer solution and the nitroxyl compounds, and measuring the signal strength by ESR after reacting the mixture for a certain period of time.

What is claimed is:

1. A nitroxyl compound of formula (I):

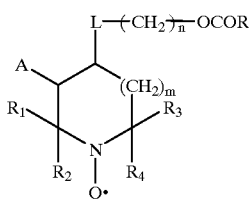

(I)

wherein A represents a hydrogen atom or the group —L—(CH$_2$)$_n$OCOR; L represents —COO— or -alkylene-COO—; R, R$_1$, R$_2$, R$_3$, and R$_4$ represent an alkyl group having 1–4 carbon atoms; m represents an integer of 0 or 1; and n represents an integer of from 1–4.

2. A pharmaceutical or chemical composition which comprises a nitroxyl compound of formula (I) as defined in claim 1 and a pharmaceutically or chemically acceptable carrier.

3. A method of treating a disease or disorder caused by active oxygen or free radicals in a mammal, comprising administering to a mammal in need thereof an effective amount of the nitroxyl compound of formula (I) as defined in claim 1.

4. The method of claim 3 wherein the disease or disorder is selected from the group consisting of ischemia, digestive diseases, cancer, cranial nervous diseases accompanied by nerve degeneration, inflammation, cataracts and drug-induced organopathy.

5. The method of claim 3 wherein the mammal is a human.

6. The method of claim 3 wherein the cancer is a brain tumor.

7. The method of claim 3 wherein the ischemia is cerebral ischemia.

8. A method of scavenging active oxygen or free radicals in a mammal comprising administering to the mammal an effective amount of the nitroxyl compound of formula (I) as defined in claim 1.

9. A method of diagnosing a disease or disorder caused by active oxygen or free radicals in a mammal, which method comprises administering to the mammal an effective amount of the nitroxyl compound of formula (I) as defined in claim 1 and then detecting a signal change of the nitroxyl compound using a magnetic resonance method.

10. The method of claim 9 wherein the magnetic resonance method is selected from the group consisting of MRI, ESR-CT and magnetoencephalogram.

11. The method of claim 9 wherein the disease or disorder is selected from the group consisting of ischemia, digestive diseases, cancer, cranial nervous diseases accompanied by nerve degeneration, inflammation, cataracts and drug-induced organopathy.

12. The method of claim 9 wherein the mammal is a human.

13. The method of claim 9 wherein the cancer is a brain tumor.

14. The method of claim 9 wherein the ischemia is cerebral ischemia.

15. A method of detecting active oxygen or free radicals in vivo, which method comprises administering to a mammal an effective amount of the nitroxyl compound of formula (I) as defined in claim 1 and then detecting a signal change of the nitroxyl compound using a magnetic resonance method.

16. The method of claim 15 wherein the mammal is a human.

17. The method of claim 14 wherein the signal change is detected using ESR.

18. The method of claim 14 wherein the signal change is detected using NMR.

19. A method of detecting active oxygen or free radicals in a biological sample in vitro, which method comprises adding an effective amount of the nitroxyl compound of formula (1) as defined in claim 1 to the sample and then detecting a signal change of the nitroxyl compound using ESR.

* * * * *

UNITED STATES PATENT AND TRADEMARK OFFICE
CERTIFICATE OF CORRECTION

PATENT NO. : 6,239,145 B1
DATED : May 29, 2001
INVENTOR(S) : Utsumi et al.

It is certified that error appears in the above-identified patent and that said Letters Patent is hereby corrected as shown below:

<u>Title page,</u>
Item [73], the Assignee's name should read:

-- [73]   Assignee:   Daiichi Radioisotope Laboratories, Ltd., Tokyo (JP) --

<u>Column 1,</u>
Line 5, first paragraph should read:

-- This is a 371 of PCT/JP98/02868 filed Jun. 26, 1998. --

Signed and Sealed this

Twelfth Day of February, 2002

*Attest:*

JAMES E. ROGAN
*Attesting Officer*   *Director of the United States Patent and Trademark Office*